United States Patent [19]

Sneath

[11] Patent Number: 5,264,344
[45] Date of Patent: Nov. 23, 1993

[54] METHOD FOR CULTURING OF CELLS ON A MEMBRANE

[75] Inventor: Peter H. A. Sneath, Leicester, United Kingdom

[73] Assignee: University of Leicester, Leicester, United Kingdom

[21] Appl. No.: 752,453

[22] PCT Filed: Feb. 28, 1990

[86] PCT No.: PCT/GB90/00316
§ 371 Date: Nov. 1, 1991
§ 102(e) Date: Nov. 1, 1991

[87] PCT Pub. No.: WO90/10056
PCT Pub. Date: Sep. 7, 1990

[30] Foreign Application Priority Data

Mar. 4, 1989 [GB] United Kingdom ............... 8905001

[51] Int. Cl.⁵ ............... G01N 33/569; C12Q 1/24; C12N 1/04; C12M 1/18
[52] U.S. Cl. ............... 435/7.32; 435/30; 435/71.1; 435/240.23; 435/285; 435/297; 435/300
[58] Field of Search ............... 422/102, 104; 435/7.32, 435/7.21, 30, 32, 34, 41, 70.1, 71.1, 240.23, 285, 300, 297, 299, 284, 301

[56] References Cited

U.S. PATENT DOCUMENTS

| | | | |
|---|---|---|---|
| 4,326,028 | 4/1982 | Brown | 435/32 |
| 4,485,171 | 11/1984 | Ikeda et al. | 435/30 |
| 4,490,466 | 12/1984 | Horwath | 435/22 |
| 4,537,860 | 8/1985 | Tolbert et al. | 435/240 |
| 4,661,458 | 4/1987 | Berry et al. | 435/284 |
| 4,673,638 | 6/1987 | Grosch et al. | 435/34 |
| 4,761,378 | 8/1988 | Godsey | 435/293 |
| 4,801,548 | 1/1989 | Takakura et al. | 435/301 |
| 4,975,377 | 12/1990 | Key | 435/284 |

FOREIGN PATENT DOCUMENTS 0062457 10/1982 European Pat. Off.
2175313 11/1986 United Kingdom.

*Primary Examiner*—Esther L. Kepplinger
*Assistant Examiner*—Nancy J. Parsons
*Attorney, Agent, or Firm*—Oblon, Spivak, McClelland, Maier & Neustadt

[57] ABSTRACT

There is disclosed a method of culturing cells which produce products and identifying the thereby produced products, characterized in that the cells are cultured on the surface of a quantity of growth medium, which surface has been divided into a plurality of growth areas thereby limiting the amount of growth-medium which is available to the cells so that these reach metabolic stage in which said products are produced, and identifying the thereby produced products by an in situ screening procedure.

27 Claims, 2 Drawing Sheets

METHOD FOR CULTURING OF CELLS ON A MEMBRANE

This invention relates to cell culture.

It is to be understood that the terms "growth" and "proliferation" when applied to cells are synonymous for the purposes of this disclosure.

Both prokaryotic and eukaryotic cells are capable of producing materials of immense pharmaceutical and industrial value. These materials may be monoclonal antibodies produced by eukaryotic hybridoma cells, or products of genes of eukaryotic origin expressed in prokaryotic cells and secreted or otherwise obtained therefrom, or indeed products of prokaryotic origin, properly expressed by and secreted from such organisms without the intervention of manipulative recombinant nucleic acid methodology.

The metabolic state of such cells is important in determining the production and excretion of such products.

For example, many common micro-organisms generally only produce and secrete such products when they have been induced to enter a phase of growth-arrest, which may be elicited by, amongst other things, nutrient depletion, competition with other micro-organisms either for nutrients or oxygen, environmental changes in the microbial habitat or by the production of antimetabolites from a different strain of micro-organism growing in the vicinity.

Examples of products which growth-arrested micro-organisms produce are antibiotics, anti-tumour agents such as mitomycin C, citrates, and heat stable enzymes which can, for example, be used in washing powders.

Initial screening procedures for cultures of micro-organisms which are potentially capable of producing such products may involve inoculating a suitable growth-medium with a crude suspension of, for example, soil. The growth medium is incubated under appropriate conditions and mixed cultures of micro-organisms are obtained. Unless these are induced to enter growth-arrest they generally will not produce, or at least excrete. appreciable quantities of useful microbial products. Moreover, in such screening procedures, a considerable quantity of growth-medium and a large number of culture vessels can be wasted through colonies not being growth-arrested and thus over-growing themselves, or over-growing nearby colonies.

Conventionally, colonies of micro-organisms, including mixed colonies containing a number of strains which additionally may have different growth rates on the same medium, reach growth-arrest slowly, but once arrested yield a dense heterogeneous mass from which it is difficult, if not impossible, to identify strains of micro-organisms of interest by use of an in situ screening procedure.

According to the present invention there is provided a method of culturing cells which produce products encouraging the cells to produce the products and identifying the thereby produced products, characterised in that the cells are cultured on the surface of a quantity of growth medium, which surface has been divided into a plurality of growth areas thereby limiting the amount of growth-medium which is available to the cells so that these reach a metabolic stage in which said products are produced. and identifying the thereby produced products by an in situ screening procedure.

The growth medium available to the cells may be limited by bounding the area of surface of growth medium available to the cells.

The area of surface of growth medium may be bounded by a membrane in contact with the surface.

The membrane may comprise a plastic film material which may be substantially impermeable to oxygen.

The plastics film material may be polyethene.

The membrane may, however, comprise a metallic material.

The membrane may have a plurality of spaced apart apertures defining areas of growth medium surface on which the cells can be grown.

The membrane may comprise a backing-layer which serves to rigidify same.

The membrane may be multilaminate in which a plurality of membranes may be superimposed upon and bonded to a semipermeable sheet. Said sheet may itself be multilaminate and may be impermeable to proteins and molecules of like-size.

The membrane may be adapted to be retained in a Petri dish or any other suitable container used in cell culture, whether such culture be of bacterial, animal or plant cells.

Preferably the apertures define an area of between 0.8 and 113 square millimeters.

More preferably the apertures define an area of between 0.8 and 51 square millimeters and most preferably the apertures define an area of between 3 and 13 square millimeters.

The apertures may be substantially of circular cross section and may be spaced between 6 and 10 millimeters apart.

The apertures may be positioned on the membrane in rows or columns, whereby a regular square arrangement of apertures in the membrane may be provided.

Each membrane may be uniquely identifiable, for example. by being numbered serially.

The serial number may be applied to the membrane in a non-toxic coloured material printed onto the surface of the membrane which contacts the medium and is thereby partially transferred thereto by which the growth-medium likewise may be numbered.

The membrane may comprise means for orientating same by which, once the membrane has been removed from the surface of the growth medium. colonies of cells remaining attached to the membrane at the periphery of the apertures therein can be located from the corresponding colonies remaining on the growth medium.

Said means may be provided by cut out sections in the membrane. The membrane may have a projection to facilitate aseptic lifting and lowering thereof on to the growth medium surface.

Preferably, however, said means comprises a grid of a non toxic coloured material applied to the surface of the membrane which contacts the medium and is thereby partially transferred thereto.

A detergent may be added to the coloured material to assist transfer thereof to the growth medium.

Said detergent may be a polyoxyethylenesorbitan, preferably the monolaurate derivative thereof.

Said non-toxic coloured material may be an Indian ink, such as Pelican Fount Indian Ink.

A stack of such membranes may be used to produce multiple copies of cultures of cells. Cells may be grown in the apertures of the membrane which define areas of growth medium. When an area of growth medium is confluent with cell growth the stack of membranes may be dismantled and the membranes may be used to inoculate further supplies of growth medium.

A stack of membranes may be treated with a release agent, such as, for example, a siliconising agent.

Screening for cell products may comprise applying an indicator agent over colonies thereof and immobilising the indicator agent whereby changes in the indicator agent around said colonies may be detected and indicate the production of said products.

The indicator agent may be a micro-organism, or it may be a chemical indicator.

Alternatively, and/or additionally, said products may be detected by immunological means whereby, for example, said products react with antibodies or indeed antigens in the case where said products are themselves antibodies.

Said antibodies or antigens may be labelled. Said labelling may be with a fluorescent marker, or any other suitable marker.

The metabolic stage of the cells may be growth-arrest, and the cells may be prokaryotic.

Where the cells are prokaryotic and the metabolic stage is growth arrest, the indicator agent may be a micro-organism such as *E. coli* which may be immobilised in soft agar, or it may be a chemical agent. The chemical agent may be applied in soft agar or in another manner such as a spray if the chemical reaction between indicator and anti-metabolite, or other microbial product can be detected in the growth medium below the micro-organism.

The indicator agent may be a chromogenic substrate added to the medium surrounding the growth arrested micro-organisms.

Screening growth arrested micro-organisms for their production of specific enzymes, for example, may comprise applying a mutant indicator cell line, which may be a mutant form of *E. coli*, in soft agar, over the growth-arrested micro-organisms. The mutation in the cell line may be such that the mutant cells are unable to grow in medium not supplemented with factors, such as enzymes, sugars or amino acids. If the growth-arrested micro-organisms produce factors required for growth of the mutant cell line, the mutant cells will grow and can be detected.

The invention will be further apparent from the following description, with reference to the several figures of the accompanying drawings, which show, by way of example only, one form of method embodying the invention, and apparatus for carrying out the method.

Figure 1:
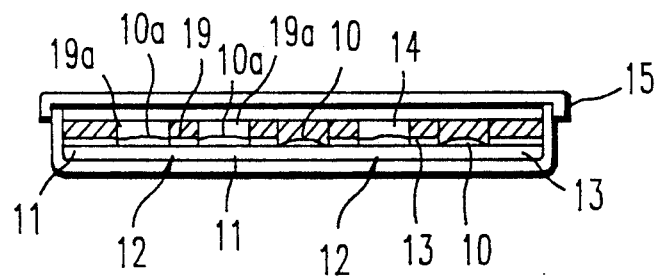
FIG. 1 is a section through a Petri dish containing a membrane bounding areas of growth medium.

The drawings illustrate a method of culturing cells so that they can produce identifiable products, characterised in that the cells 10 are cultured on the surface of a quantity of growth medium 11, which surface has been divided into a plurality of growth areas 12 thereby limiting the amount of growth medium 11 which is available to the cells 10 so that the cells 10 reach a metabolic stage in which said products are produced, and identifying the thereby produced products by an in situ screening procedure.

The growth medium available to the cells is limited by bounding the area of surface of growth medium available to the cells 10.

The surface area of growth medium 11 is bounded by a membrane 13 in contact with the surface.

The membrane 13 comprises a plastic film material, such as polyethene, which is substantially impermeable to oxygen. Preferably the surface of the membrane, other than the surface which contacts the growth medium, has a waxy characteristic, whereby moisture is substantially prevented from spreading thereon.

It will be appreciated however, that membranes according to the invention comprised by a metallic material, such as an aluminium wafer, might suggest themselves to specific applications.

The membrane 13 has a plurality of spaced apart apertures 14 defining the areas 11 of growth medium surface on which the cells 10 are grown.

The membrane 13 is adapted to be retained in a Petri dish 15 perhaps of 10 cm diameter or any other suitable container used in cell culture, whether this be bacterial, animal or plant cell culture.

The apertures 14 each define an area of between 0.8 and 113 square millimeters, more preferably an area of between 0.8 and 51 square millimeters and most preferably an area of between 3 and 13 square millimeters.

Figure 2:
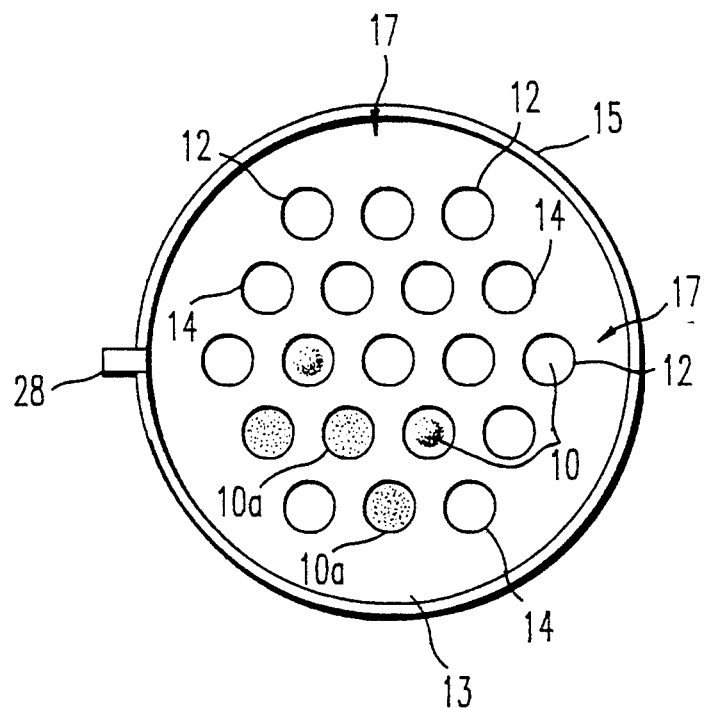
FIG. 2 is a plan of the Petri dish illustrated in FIG. 1.
Figure 3:
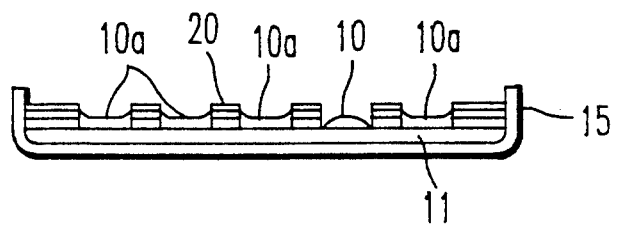
FIG. 3 is a section through another Petri dish containing a stack of membranes.

As shown in FIG. 2, the apertures are substantially of circular cross section.

The apertures 14 are spaced between 6 and 10 millimeters apart, although several spacings are contemplated according to the application (see below).

Figure 4:
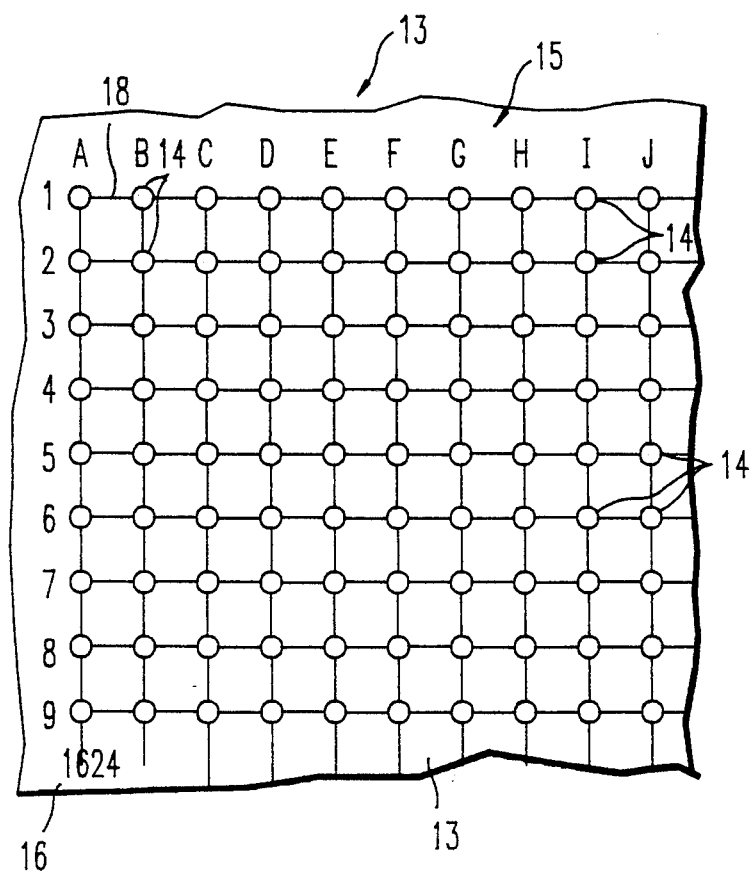
FIG. 4 shows the preferred disposition of apertures in a membrane.

The apertures 14 are positioned on the membrane 13 in rows or columns, whereby a regular square arrangement 15 of apertures 14 on the membrane 13 provided, as shown in FIG. 4.

It is preferred that a face centred square arrangement (quincunx) be avoided in applications where the membranes are treated with a transferable ink for orientating same on the surface of growth medium (see below).

Each membrane is uniquely identifiable, by being numbered serially 16. Such identification is provided in a form which is transferable from the membrane to the surface of the growth medium, and also in a form which is retained on the membrane 13.

The serial number 16 is applied to the membrane by a non-toxic coloured material being applied to the surface of the membrane 12 which contacts the medium and which is thereby partially transfered thereto, and by which the growth medium is likewise numbered. The same number is applied to the non-contacting surface of the membrane in an indelible ink.

The membrane may be orientated with respect to a surface of the growth medium with which previously it had been in contact whereby colonies of cells remaining thereon can be identified from the corresponding apertures in said membrane.

The membrane may be orientated by providing cut out sections 17 in the membrane, which section correspond to particular points on the growth medium surface. The membrane has a projection 28 to facilitate aseptic lifting and lowering of same onto the growth medium surface.

Preferably, however, a grid 18 of a non toxic coloured material such as an indian ink (Pelican Fount Indian Ink) is applied to the surface of the membrane 13 which contacts the medium 11 and is thereby partially transferred thereto. Rows and columns of the grid 18 may be lettered or numbered in the same ink.

A detergent is added to the ink to aid partial transfer thereof to the growth medium surface.

The detergent is biologically relatively benign, and preferably is the monolaurate derivative of polyoxyethylenesorbitan.

The non-contacting surface of the membrane 13 may carry a similar grid, similarly lettered or numbered, in indelible ink.

A stack 20 of membranes 13 is used to produce multiple copies of cultures of cells. In use the cells are grown on a growth medium 11 surface until they reach the boundary of surface of growth medium imposed by the apertures in the stack of membranes. Cell growth is arrested by limitation of the medium available to the cells. As the cells fill the apertures the stack of membranes becomes contaminated around the apertures. The stack of membranes is dismantled and the individual membranes used to inoculate further supplies of growth-medium.

The stack 20 of membranes 13 is treated with a release agent, such as, for example, a siliconising agent.

Screening for cell products comprises application of an indicator agent 19 over colonies thereof and immobilising the indicator agent 19 whereby changes in the indicator agent shown at 19a around said colonies may be detected and indicate the production of said products.

The indicator agent 19 may be a micro-organism, or it may be a chemical indicator.

Alternatively, or additionally, said products may be detected by immunological means whereby, for example, said products react with antibodies or indeed antibodies or antigens in the case where said products are themselves antibodies.

Said antibodies or antigens may be labelled with a fluorescent, or any other suitable marker.

In the case where the cells are growth-arrested microbial cells the screening method comprises applying an indicator agent 19 over colonies of growth-arrested micro-organisms and immobilising the indicator agent whereby changes in the indicator agent shown diagrammatically at 19a in FIG. 1 around the colonies of growth arrested micro-organisms may be detected to indicate the production of useful microbial products.

In practice the indicator agent might be a micro-organism such as *E. coli* which can be immobilised in soft agar. Anti-metabolites, or other microbial products, could be demonstrated by areas of reduced growth of lysis of the *E. coli* indicator around the growth arrested product producing micro-organisms 10a. For example, this may appear as a clear area 19a, in the agar containing the *E. coli*, around the colonies of growth-arrested micro-organisms 10a which are producing products. Where the indicator micro-organisms are able to grow around colonies not producing anti-metabolites the agar will be opaque.

It will be appreciated, however, that the indicator could be a chemical agent such as a dye which binds preferentially to microbial products and which can be detected by means of a colourimetric reaction.

The chemical agent can be applied in soft agar or in another manner, such as a spray, if the chemical reaction between the indicator and anti-metabolite, or other microbial product can be detected in the growth medium below the micro-organism.

Natural products, such as enzymes, produced by the growth arrested micro-organisms, can be detected by addition of a chromogenic substrate to the medium surrounding the growth-arrested micro-organisms. For example, nitrocefin can be added to the growth medium, facilitating the detection of, for example, the microbial production of penicillinase since, when penicillinase reacts with nitrocefin, the nitrocefin, otherwise yellow, turns red.

Screening for enzymes and other natural products may comprise applying a mutant indicator cell line, which can be a mutant form of *E. coli*, in soft agar, over the growth arrested micro-organisms. The mutation in the indicator cell line is such that the mutant cells are unable to grow in medium not supplemented with factors. If the growth-arrested micro-organisms produce factors required for growth of the mutuant cell line, the mutant cells will grow and can be visualised. The factors may comprise enzymes, which restore an enzyme deficiency in the mutant indicator cells or they may comprise a metabolite such as a sugar or amino acid which the mutant indicator cells require for growth.

In a further embodiment, the indicator cell line may be such that a defined reagent is toxic to, or otherwise inhibits, growth of the indicator cells. The reagent may be added to the soft agar in which the indicator cells are layered onto the growth-arrested micro-organisms. The reagent, for example, may be an antibiotic or chemically modified antibiotic. Microbial products produced by growth-arrested micro-organisms, may cleave, or otherwise-modify the reagent, thus enabling the indicator cells to grow. Growth, rather than lysis, of the indicator cells is then evidence of the production by the growth-arrested micro-organisms of a defined class of microbial products. A mutation may be made in the indicator cell line so that the indicator cells become susceptible to the reagents.

Multiple screening of a single colony of growth-arrested micro-organisms can be carried out. By having, for example, an indicator agent in the growth medium and a different indicator agent in soft agar which is then layered on to the growth arrested micro-organisms, it is possible to detect the production of two different microbial products.

Use of membranes according to the invention increases the speed of work involving numerous micro-organisms or cells, and increases the likelihood that each aperture contains a pure, or substantially pure culture.

Use of the membranes enables automation and standardisation of techniques involving cell culture in industrial processes. Use of the membranes aids automatic inoculation aspects and automatic detection of required cell products by restricting cell growth chiefly to designated positions, which are explicitly numbered (or have implied numbered positions by row and column).

Where the cells seeded into the apertures in the membranes are eukaryotic, for example antibody-producing hybridomas, the membrane preferably is positioned on the surface of a collagen or gelatin substrate, although any other suitable solid support media may be used, including fibrin and agar or agarose gels, or suitable derivatives thereof.

In practice, the membrane is placed onto the solid support medium which contains suitable nutrients.

A mixed population of antibody-producing cells is then inoculated into the medium, at a dilution which provides for an average of rather less than one viable cell per aperture. The cells are grown and the membrane is then removed to a second growth medium so as to preserve alive the various clones adhering to the periphery of the apertures in the membrane, and the first medium is tested for a cell product.

Where the product is an antibody, the medium at the position of previous aperture sites is detected by applying a labelled antigen thereto. The antigen is labelled with a fluorescent dye, but more conveniently an indirect method is used in which antigen is added at the sites of the apertures, and second antibodies raised in an immunologically distinct organism against the antigen are fluorescently labelled and bound thereto. The desired clones are located from the corresponding aperture on the membrane now in the second growth medium, purified if necessary and grown in bulk.

Figure 5:
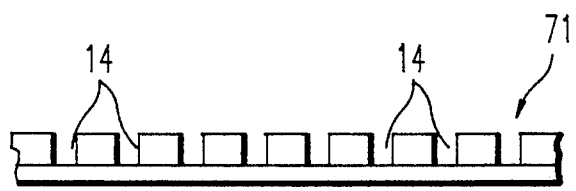
FIG. 5 shows a membrane according to the invention comprising a backing material which contacts the surface of growth medium.

The membrane 71 may comprise a backing layer 72 which serves to rigidify same as shown in FIG. 5.

Figure 6:
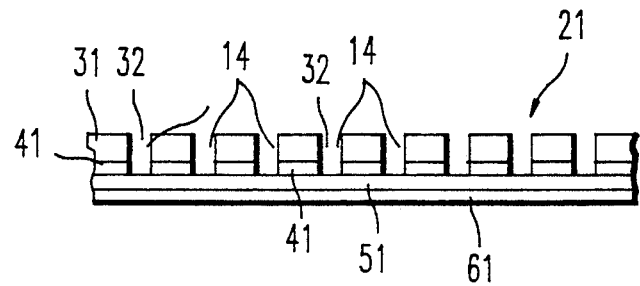
FIG. 6 shows a further form of membrane adapted for use in culture of eukaryotic cells, particularly those producing monoclonal antibodies.

Should such cells not be capable of suitable growth on said solid growth media, a modified mulilaminar membrane 21 shown in FIG. 6 is provided. This comprises a first layer comprised by a polyethene membrane 31 of relatively increased thickness so that the apertures 14 define shallow walls 32. This is superimposed upon and bonded to a semipermeable sheet 41 having apertures 14 of size and configuration corresponding to those in the first layer 31, and a pore size of perhaps 0.5 micrometers. The layer 41 is itself bonded to a further layer 51 of similar material but lacking apertures. The layer 51 is further bonded to a sheet of material 61, such as cellophane, which allows passage thereacross of small molecules such as water and vitamins etc, but prevents passage thereacross of molecules such as proteins, and particularly antibodies.

The membrane 21 comprising four layers is floated on a liquid nutrient medium, and is inoculated with cells as above, viz, at a density which gives rather less than one viable cell per aperture 14. Clones of cells result in the apertures 14, and antibodies produced thereby diffuse into the third layer 51 of the membrane 21 having a pore size of 0.5 microns but no apertures. The antibodies do not diffuse into the fourth layer 61, viz, that comprised by the cellophane-like material. After appropriate cell growth the upper membranes are transferred to a second growth medium and the lower two membranes are tested for the presence of antibodies.

The cell clones producing the desired antibody are then isolated from the corresponding apertures in the upper layers of the membrane, now in the second growth medium.

It will be appreciated that it is not intended to limit the invention to the above examples only, many variations, such as might readily occur to one skilled in the art, being possible, without departing from the scope thereof as defined by the appended claims.

For example, the multilaminate membrane can be adapted for the detection in situ of nucleic acid molecules. In this case, the upper membrane has pores large enough to enable some cells, including prokaryotic cells where appropriate, to grow downwardly into the lower layer adjacent the cellophane or like-material layer. The upper two layers comprised by the membrane are then removed and transferred to a second growth medium, whilst the cells in the lower layer are denatured and nucleic acid therein exposed to known probing regimes.

The upper layers in the multilaminate membrane may be coated with fibronectin, and like molecules to encourage cell growth.

Cells identified as useful by use of the method can be grown according to known means and the products identified by the method purified therefrom.

I claim:

1. A method of producing cell products from cells which produce said products when the cells are in a growth arrest metabolic stage, said method comprising:
   a) providing a nutrient growth medium having a surface on which cells grow,
   b) dividing the surface into a plurality of spaced apart growth areas thereby limiting the amount of growth medium so the cells reach growth arrest and produce their products, said surface being divided by contacting the surface of the medium with a removable impermeable film, said film
      1) having a plurality of spaced apart apertures defining spaced apart areas of growth medium available to the cells, and
      2) having a means of identifying and locating cells comprising a non-toxic colored material applied to the surface of the film which contacts the medium and is thereby partially transferred to the surface of the medium,
   c) culturing cells on the surface of the growth medium within the spaced apart apertures, and
   d) screening for and harvesting the cell products.

2. A method according to claim 1, wherein the film comprises a plastics material.

3. A method according to claim 2, wherein the plastics material is polyethylene.

4. A method according to claim 1, wherein the film comprises a metallic material.

5. A method according to claim 1, wherein the film is adapted to be retained in a Petri dish.

6. A method according to claim 1, wherein the apertures are substantially of circular cross section and define an area of between 0.8 and 113 square millimeters.

7. A method according to claim 6, wherein the apertures are substantially of circular cross section and define an area of between 0.8 and 51 square millimeters.

8. A method according to claim 7, wherein the apertures are substantially of circular cross section and define an area of between 3 and 13 square millimeters.

9. A method according to claim 1, wherein the apertures are spaced between 6 and 10 millimeters apart.

10. A method according to claim 1, wherein the apertures are positioned on the film in rows or columns, whereby a regular square arrangement of apertures in the film is provided.

11. A method according to claim 1, wherein the film is uniquely identifiable, by being numbered serially.

12. A method according to claim 11, wherein the serial number is applied to the film in said non-toxic colored material and is thereby partially transferred to the medium.

13. A method according to claim 10, wherein said non-toxic colored material is in the form of a grid and the rows and columns are numbered or lettered.

14. A method according to claim 1, wherein a detergent is added to the colored material to assist transfer thereof to the growth medium.

15. A method according to claim 14, wherein said detergent is a polyoxyethylenesorbitan.

16. A method according to claim 1, wherein said non-toxic colored material is an Indian ink.

17. A method according to claim 1, wherein a stack of said films is used to produce multiple copies of cultures of cells, so that when an area of growth medium defined by apertures in the films is confluent with cell growth the stack of films can be dismantled and cells remaining attached to the films at the periphery of the apertures are transferred when the films are used to inoculate further supplies of growth medium.

18. A method according to claim 1, wherein the screening for cell products comprises applying an indicator agent over colonies located in the apertures of the film whereby changes in the indicator agent around said colonies may be detected and indicate the production of said products.

19. A method according to claim 18, wherein the indicator agent is a micro-organism.

20. A method according to claim 18, wherein said indicator agent is a chemical indicator.

21. A method according to claim 18, wherein said indicator agent is applied in soft agar to the cells.

22. A method according to claim 20, wherein said indicator is applied to the cells as a spray wherein a chemical reaction between indicator and product can be detected in the growth medium below the cells.

23. A method according to claim 20, wherein the indicator agent is a chromogenic substrate added to the medium.

24. A method according to claim 18, wherein said products are detected by immunological means whereby the indicator agent comprises antibodies or antigens which react with said products.

25. A method according to claim 24, wherein said antibodies or antigens are labelled.

26. A method according to claim 25, wherein the label is a fluorescent dye.

27. A method according to claim 1, wherein the cells are prokaryotic.

* * * * *

UNITED STATES PATENT AND TRADEMARK OFFICE
CERTIFICATE OF CORRECTION

PATENT NO. : 5,264,344
DATED : November 23, 1993
INVENTOR(S) : Peter H.A. Sneath It is certified that error appears in the above-indentified patent and that said Letters Patent is hereby corrected as shown below:

On the title page, Item [54] and Column 1, Line2,

The title should read: --METHOD FOR CULTURING CELLS TO PRODUCE PRODUCTS ON A LIMITED AREA OF GROWTH MEDIUM DEFINED BY A REMOVABLE IMPERMEABLE FILM--

Signed and Sealed this

Seventeenth Day of May, 1994

Attest:

BRUCE LEHMAN

Attesting Officer     Commissioner of Patents and Trademarks